(12) United States Patent
Purmal et al.

(10) Patent No.: US 6,720,136 B2
(45) Date of Patent: **\*Apr. 13, 2004**

(54) SOLID PHASE QUENCHING SYSTEMS

(75) Inventors: Andrei A. Purmal, Waltham, MA (US); Samuel K. Ackerman, Weston, MA (US)

(73) Assignee: V. I Technologies, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/166,898

(22) Filed: Jun. 11, 2002

(65) Prior Publication Data

US 2002/0150950 A1 Oct. 17, 2002

Related U.S. Application Data

(63) Continuation of application No. 09/161,078, filed on Sep. 25, 1998, now Pat. No. 6,403,359.

(51) Int. Cl.⁷ .................................................. C12N 7/06
(52) U.S. Cl. ........................ 435/2; 435/238; 422/28; 210/660
(58) Field of Search ...................... 435/2, 238; 210/660; 422/28

(56) References Cited

U.S. PATENT DOCUMENTS

| | | | |
|---|---|---|---|
| 3,487,157 A | 12/1969 | Pierce et al. | |
| 3,492,289 A | 1/1970 | Symm et al. | |
| 3,501,557 A | 3/1970 | Brois et al. | |
| 3,636,196 A | 1/1972 | Bauer et al. | |
| 4,098,726 A | 7/1978 | Wagner et al. | |
| 4,161,581 A | 7/1979 | Wagner et al. | |
| 4,206,295 A | 6/1980 | Wagner et al. | |
| 4,371,472 A | 2/1983 | Okazaki et al. | |
| 4,429,045 A | 1/1984 | Bass et al. | |
| 4,515,906 A | 5/1985 | Friesen et al. | |
| 4,581,368 A | 4/1986 | Ahmed et al. | |
| 4,757,148 A | 7/1988 | Ahmed et al. | |
| 4,784,992 A | 11/1988 | Reiner | |
| 4,841,023 A | 6/1989 | Horowitz | |
| 5,000,951 A | 3/1991 | Bass et al. | |
| 5,055,485 A | 10/1991 | Geacintov et al. | |
| 5,120,649 A | 6/1992 | Horowitz et al. | |
| 5,232,844 A | 8/1993 | Horowitz et al. | |
| 5,374,424 A | 12/1994 | Kelsey et al. | |
| 5,418,130 A | 5/1995 | Platz et al. | |
| 5,547,576 A | 8/1996 | Onishi et al. | |
| 5,559,250 A | 9/1996 | Cook et al. | |
| 5,691,132 A | 11/1997 | Wollowitz et al. | |
| 5,698,432 A | 12/1997 | Oxford | |
| 5,736,624 A | 4/1998 | Bieniarz et al. | |
| 5,891,705 A | 4/1999 | Budowsky et al. | |
| 6,093,564 A | 7/2000 | Budowsky et al. | |
| 6,093,725 A | 7/2000 | Cook et al. | |
| 6,114,108 A | 9/2000 | Budowsky | |
| 6,136,586 A | 10/2000 | Budowsky | |
| 6,143,490 A | 11/2000 | Cook et al. | |
| 6,171,777 B1 | 1/2001 | Cook et al. | |
| 6,177,441 B1 | 1/2001 | Cook et al. | |
| 6,270,952 B1 | 8/2001 | Cook et al. | |
| 6,352,695 B1 | 3/2002 | Budowsky et al. | |
| 6,369,048 B1 | 4/2002 | Budowsky et al. | |
| 6,403,359 B1 * | 6/2002 | Purmal et al. | |
| 6,410,219 B1 | 6/2002 | Cook et al. | |
| 2002/0034724 A1 | 3/2002 | Edson et al. | |

FOREIGN PATENT DOCUMENTS

| | | |
|---|---|---|
| EP | 0 476 711 A2 | 3/1992 |
| EP | 0612532 A2 | 8/1994 |
| JP | 53-82735 A | 7/1978 |
| JP | 6-805520 A | 3/1994 |
| RO | 101400 A | 12/1992 |
| SU | 1768636 A1 | 10/1992 |
| SU | 1809836 A3 | 4/1993 |
| SU | 594771 A1 | 7/1993 |
| WO | WO 92/03157 A1 | 3/1992 |
| WO | WO 92/04031 A1 | 3/1992 |
| WO | WO 92/18161 A1 | 10/1992 |
| WO | WO 96/14737 A1 | 5/1996 |
| WO | WO 96/39818 A1 | 12/1996 |
| WO | WO 96/39820 A1 | 12/1996 |
| WO | WO 96/40857 A1 | 12/1996 |
| WO | WO 97/07674 A1 | 3/1997 |
| WO | WO 97/21346 A1 | 6/1997 |
| WO | WO 98/30327 A1 | 7/1998 |
| WO | WO 98/30545 A1 | 7/1998 |
| WO | WO 98/45415 A1 | 10/1998 |
| WO | WO 99/17802 A1 | 4/1999 |
| WO | WO 99/34791 A1 | 4/1999 |
| WO | WO 00/18412 A1 | 4/2000 |
| WO | WO 00/18969 A1 | 4/2000 |

OTHER PUBLICATIONS

US 6,331,387, 12/2001, Hei et al. (withdrawn)
Ackerman, et al. "Inactine™—A Potent and Selective Method for Inactivating Viruses in Contaminated Blood Products.", *25th Congress of the International Society of Blood Transfusion*, Jun. 27–Jul. 2, 1998, Oslo, Norway. Abstract No. 1305.
Amor, S,, and H.E.Webb, Use of N–Acetylethyleneimine [AEI] for the inactivation of Semliki Forest Virus in vitro J Medical Virology 19:367–376 (1986).

(List continued on next page.)

Primary Examiner—Leon B. Lankford, Jr.
(74) Attorney, Agent, or Firm—Wolf, Greenfield & Sacks, P.C.

(57) ABSTRACT

Methods of inactivating contaminants of a biological matrix are disclosed. The methods include the steps of: (a) contacting a biological matrix with an inactivating agent including an aziridino moiety, where a portion of the agent reacts with and inactivates the contaminant, and a portion of the agent remains unreacted; (b) contacting the product of step (a) with a solid support including at least 1 quenching moiety attached to the solid support through covalent bonds, under conditions and for a time sufficient to allow the unreacted agent to bond covalently to the quenching moiety; and (c) separating the solid support and the unreacted agent from the biological matrix, where the unreacted agent is attached to the solid support through covalent bonds.

7 Claims, 7 Drawing Sheets

OTHER PUBLICATIONS

Atwell, G.J. et al.. Synthesis, DNA Interactions and Biological Activity of DNA Minor Groove Targeted Polyberizamide–linked Nitrogen Mustards, Bloorg Med. Client. Jun. 1995; 3(6):679–91.

Bahnemann, "Inactivation of viral antigens for vaccine preparation with particular reference to the application of binary ethylenimine" Vaccine 8:299–303 (1990).

Bahnemann, H.G., Inactivation of Viruses in Serum with Binary Ethyleneimine, Journal of Clinical Microbiology, vol. 3, No. 2, pp. 209–210 (1975).

Bieniarz et al., "A facile, high–yielding method for the conversion of halides to mercaptans" Tetrahedron Lett. 34:939–942 (1993).

Briel, S. et al Identification of New Aqueo Chemical Degradation Products of Isophosphoramide Mtard J Pharm Biomed Anal. Jun. 2001;25 (3–4): 669–78.

Brown, F. et al. A Universal Virus Inactivant for Decontaminating Blood and Biopharmaceutical Products Biologicals (1998) 26, 39–47.

Budowsky and Zalesskaya, "Principles of selective inactivation of viral genome. V. Rational selection of conditions for inactivation of the viral suspension infectivity to a given extent by the action of B–propiolactone" Vaccine 9:319–325 (1991).

Budowsky et al., "Inactivation of the phage MS2 infectivity by the action of ethyleneimines" Biorg. Khim. 11:989–991 (1985)(in Russian). English Abstract provided, 1 page.

Budowsky et al., "Principles of selective inactivation of the viral genome; dependence of the rate of viral RNA modification on the number of protonizable groups in ethyleneimine oligomer" Vaccine Res. 5:29–39 (1996).

Budowsky, E.I., Problems and prospects for preparation of killed antiviral vaccines Adv. Vir Res. 39:255–90 (1991).

Charache, S. et al.. Evaluation of Extracorporeal Alkylation of Red Cells as a Potential Treatment for Sickle Cell Anemia, Blood 1976; 47(3):481–88.

Creech et al., "Antitumor and mutagenic properties of a variety of heterocyclic nitrogen and sulfur mtards" Med. Chem. 15: 739–746 (1972).

Danao, T. et al., Nitrogen Mtard as Induction Therapy for Rheurnatoid Arthritis: Clinical and Immunologic Effects. J. Rheum. 1992 19:1683–86.

Dermer and Ham, Ethyleneimine And Other Aziridines, Acad. Press, NY—London (1969), pp. 249–285.

Drake, M.E. et al., Effect of Nitrogen Mtard on Vir of Serum Hepatitis in Whole Blood. Proc. of Soc. Exp. Rio. Med. 1952(80)310–13.

Earley et al., "Reactions and ethylenimines. IX. The mechanisms of ring openings of ethylenimines in acidic solutions" J. Am. Chem. Soc. 80:3458–3462 (1958).

Edson, et al. IBC 2nd International Symposium on Viral Clearance, Jun. 25–26, 1998., INACTINE™—An Inactivation Technology for Reducing the Viral Infectivity of Plasma–Derived Proteins and Red Blood Cells.

Ferguson, L.R. et al.. DNA–directed Aniline Mustards with High Se lectivity for Adenine or Guanine Bases: Mutagenesis in a variety of Salmonella Typhimurium Strains Differing in DNA–Repair Capability, Mutat Res. Apr. 1994; 321(1–2):27–34.

Ferguson, L.R. et cal.. Bacterial Mutagenicity Studies of DNA–Intercalating Aniline Mustards: an Insight Into the Mode of Action of a Novel Class of Anti–Tumor Drugs, Anticancer Drug Des. Oct. 1989; 4(3):209–19.

Fries, K.M. et al 31P NMR and Chloride Ion Kinetics of Alkylating Monoester Phosphoramidates J. Med. Chem Feb. 1991;34(2): 565–9.

Gao. Yi–Gui; Sriram, M. et cal.. Minor Groove Binding of SN6999 to an Alkylated DNA: Molecular Structure of d(CGC[e6G]AATTCGCG)–SN6999 Complex, Biochemistry Sep. 21, 1993; 32(37):9639–48.

Gourdie T.A. et al.. DNA–directed Alkylating Agents. 1. Structure–activity Relationships for Acridine–linked Aniline Mustards: Consequences of Varying the Reactivity of the Mustard, J. Med. Chem. Apr. 1990; 33(4):1177–86.

Gourdie T.A. et al.. Synthesis and Evaluation of DNA–targeted Spatially Separated Bis(Aniline Mustards) as Potential Alkylating Agents with Enhances DNA Cross–linking Capability, J. Med. Chem. Jan. 1991; 34(1):240–8.

Gravatt, G.L. et al., DNA–directed Alkylating Agents. 6. Synthesis and Antitumor Activity of DNA Tumor Groove–targeted Aniline Mustard Analogues of Pibenzimol, J. Med. Chem.. Dec. 9, 1994; 37(25): 4338–45.

Gravatt, G.L. et al.. DNA–Directed Alkylating Agents 4. 4–Anilinoduinoline–Based Minor Groove Directed Aniline Mustards, J. Med Chem 1991, 34(5):1552–60.

Griffin M.T. et al Kinetics of Activation and in Vivo Muscarinic Receptor Binding of N–(2–bromoethyl)–4–Piperidinyl Diphenylacetate: an Analog of 4–DAMP Mustard J. Pharmacol Exp Ther Jul. 1993; 266(1) 301–5.

Hagen et al., "Chemical modification of polystyrene introduction of sulfinate and sufone functionalities" Polymer Bull. 5:111–116 (1981).

Hamza, A. Quantum Molecular Modeling of the Interaction Between Guanine and Alkylating Agents—2–Nitrogen Mustard J. Biomol Struct Dyn Jun. 1996; 13(6):915–24.

Hartman, F.W. et al., Preparation and Sterilization of Blood Plasma. Ant. J. Clin. Path, 1954(24); 339–48.

Hartman, F.W. et al.. On the Chemical Sterilization of Blood and Blood Plasma. Proc. of Soc.. Exp. Bio. Med. 1949;70:248–54.

Hartman, F.W., et al.. Four–Year Study Concerning the inactivation of Viruses in Blood and Plasma, Presented at the 55th Annual Meeting of the American Gastroenterological Association, San Francisco, California, Jun. 1954.

Hassanain, M.M., Preliminary findings for an inactivated African horsesickness vaccine using binary ethyleneimine Revue Elev. Med. Vet. Pays Trop. 45: 231–234 (1992).

Hemminki, K. DNA Adducts of Nitrogen Mtards and Ethyleneimines DNA Adducts: Identification and Biological Significance, IARC Scientific Publications No. 125, Editors: Hemminki, et al., 1994, pp. 313–321.

Hemminki, K. Reactions of Nitrogen Mustards with DNA IARC Sci. Publ 1986; (78):55–70.

King, et al. "Evaluation of different methods of inactivation of newcastle disease virus and avian influenza virus in egg fluids and serum" Avian Diseases 35:505–514 (1991).

Knorre, D.G. et al.. Reactive Derivatives Of Oligonucleotides As Potential Antiviral Drugs, Problems of Virology, 1985, No. 5, pp. 524–'?.

Kochetkov and Budowsky eds., Organic Chemistry of Nucleic Acids, Part A,Plenum Press, London–New York, pp. 48–55 (1972).

Kohn, K.W. et al Mechanisms of DNA Sequence Selective Alkylation of Guanine–N7 Positions by Nitrogen Mustards Biochem Pharmacol May 1, 1988; 37(9): 1799–800.

Kostyanovskii et al., "Oligomers of azridines and N–beta–azridinoethylamides," Bull. Acad. Sci. SR, Div. Chem. Sci., 37:2315–2325 (1989). (Translated from IzvestiyaAkademi Nauk SSSR, Seriya Khimicheskaya 11:2566–2575.).

Lee, M et al., In Vitro Cytotoxicity of GC Sequence Directed Alkylating Agents Related to Distamycin, J. Med. Cheer. Apr. 2, 1993; 36(7)863–70.

Lobastov, A.E., e of ethylenimine dimmer for the inactivation of infectio rhinotracheitis virus of cattle Probl. Virol., Mol. Biol. Gistol. S–kh. Zhivotn., pp. 4–6 (1983) (English translation).

Logrippo, G.A et al.. Chemical and Combined Methods for Plasma Sterilization., 6th Congress of the Int'l Soc. of Blood Trans., 1958, pp. 225–230.

Mattes, W.B. et al.. GC–rich Regions in Genomes as Targets for DNA Alkylation, Carcinogenesis 1988; 9(11):2065–72.

Prakash, A.S. et al., Differences in Sequence Selectivity of DNA Alkylation by Isomeric Intercalating Aniline Mustards, Chem. Biol. Interact. 1990; 76(23):241–8.

Price, C.C. et al Relative Reactivities for Monofunctional Nitrogen Mtard Alkylation of Nulceic Acid Components Biochim Biophys Acta Sep. 24, 1968; 166(2):327–59.

Prodouz et al., "Inhibition of merocyanine 540–mediated photosensitization of platelets and viruses" Transfusion 31:415–422 (1991).

Race et al., "An experimental chemically inactivated HIV–1 vaccine induces antibodies that neutralize homologo and heterologo viruses" Vaccine 13:54–60 (1995).

Roth, E.F. Jr. et al., Metabolic Effects of Antisickling Amounts of Nitrogen and Nor–N itrogen Mustard on Rabbit and Human Erythrocytes. Blood 1975;45(6):779–88.

Springer, J.B. et al Isophosphoramide Mustard and Its Mechanism of Bisalkylation J. Org. Chem Oct. 16, 1998; 63(21):7218–7222.

Tanirbergenov et al., "Regularities of mutagenic and toxic effects of ethyleneimine and its oligomers. A comparative study in the automated system SOS–chromotest and in standard bacterial test systems" Genetika 24:763 (1988) (in Russian). English translation provided, 5 pages.

Thanei–Wyss, "Interaction of quaternary ammonium compounds with acetylcholinesterase: characteristics of the active site" Eur. J. Pharmacol., Mol. Pharmacol. Sect. 172:165–173 (1989).

Twomey et al., "Structure and immunogenicity of experimental foot–and–mouth disease and poliomyelitis" Vaccine 13:1603–1610 (1995).

Valu, K.K. et al., DNA–directed Alkylating Agents. 3. Structure–activity relationships for Acridine–linked Aniline Mustards: Consequences of Varying the Length of the Linker Chain. J. Med. Chem Nov. 1990: 33(11):3014–9.

Van Etten and Dolhum, "Effects of hydrogen–bond formation by phenols on the conformational equilibrium of trans–1,2–dimethyl–3–isopropylaziridine" J. Org. Chem. 33:3904–3907 (1968).

Verschaeve, L. et a. "Mutagenicity of Ethyleneimine" Mutation Res. 238:39–55 (1990).

Vlasov, V.V. et al., –The Feasibility, Of Blocking Influenza Infections By Means Of Alkylating Derivatives Of Oligonucleotides, Molecular Genetics, Microbiology, And Virology, 1984, No. 11.

Wagner et al., "Approaches to the reduction of viral infectivity in cellular blood components and single donor plasma" Transfusion Med. Rev. 5:18–32 (1991).

Warrington, Derivatives of Aziridine as Inactivants for Foot––and–Mouth Disease Vir Vaccines, Am J. Vet. Res., vol. 34, No. 8. pp. 1087–1091.

Wickham, G. et al., DNA–binding Properties and Antitumour Activity of Monofunctional Alkylating Groups Attached to the DNA–intercalating Chromophore Phenanthridine: n–Brotnoalkylplienanthridinium Bromides, Biochimic et Biopysica Acta 1991 1073:528–37.

Wilke, W.S. et cal., Parenteral Nitrogen Mustard for Inflammatory Arthritis, C'lev. Clin. J. Med. Oct. 1990; 57(7):643–46.

Yamamoto, et al. Cancer Research 26, pt. 1, 2301–2306 (Nov. 1966).

Yang, C. et al The Preparation of an Inactivated Antigen for Bluetongue Serology Zentralbl Veterinarmed [B] May 1984; 31(4); 290–6.

Zalesskaya, M.A., Inactivation of viral genome by beta–propiolactone and ethyleneimines using the bacteriophage MS–2 as an example, Russian State Library, Moscow, Russia (1988).

* cited by examiner

SOLID PHASE QUENCHING SYSTEMS

CROSS-REFERENCE TO RELATED APPLICATIONS

This application is a continuation of U.S. application Ser. No. 09/161,078, filed Sep. 25, 1998, now U.S. Pat. No. 6,403,359, hereby incorporated by reference.

BACKGROUND OF THE INVENTION

The invention relates to methods for quenching electrophiles.

The transmission of viral diseases (e.g., hepatitis A, B, and C, acquired immunodeficiency syndrome, and cytomegalovirus infections) by blood or blood products is a significant problem in medicine. Screening donor blood for viral markers can help reduce the transmission of viruses to recipients, but many screening methods are directed to only a few discrete viruses and are therefore incomplete or less than 100% sensitive. Furthermore, other biological compositions, such as mammalian and hybridoma cell lines, products of cell lines, milk, colostrum, and sperm, can contain infectious viruses as well. It is therefore important to inactivate viruses contained in donor blood, blood products, or other biological compositions.

A number of agents that are capable of inactivating viruses in blood have been developed. For example, ethyleneimine monomer and ethyleneimine oligomers are very effective viral inactivating agents. These agents are themselves toxic, and must therefore be rendered non-toxic before a product, such as blood, is used clinically. Typically, a viral inactivating compound, such as ethyleneimine dimer, is added to a biological composition to inactivate infectious viruses that might be present in the composition. A quenching agent is then added to inactivate the ethyleneimine dimer that remains after viral inactivation has taken place. The end result is a biological composition that is relatively free of infectious viruses, but that is contaminated with quenched inactivating agent and with quenching agent.

SUMMARY OF THE INVENTION

In one aspect, the invention features a method of inactivating a contaminant, such as a virus, of a biological matrix; the method includes the steps of: (a) contacting the biological matrix with an inactivating agent including an aziridino moiety, where a portion of the agent reacts with and inactivates the contaminant, and a portion of the agent remains unreacted; (b) contacting the product of step (a) with a solid support including at least 1 quenching moiety attached to the solid support through covalent bonds, under conditions and for a time sufficient to allow the unreacted agent to bond covalently to the quenching moiety; and (c) separating the solid support and the unreacted agent from the biological matrix, where the unreacted agent is attached to the solid support through covalent bonds.

A preferred quenching moiety includes a nucleophilic moiety, such as a thiophosphate group; the thiophosphate group may be part of an internucleotide linkage of a oligonucleotide sequence. Preferably, the solid support contains at least 2 mmol/g thiophosphate moieties.

The inactivating agent may be, for example, ethyleneimine or an oligomer of ethyleneimine. The biological matrix may be selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture medium, a placental extract, a product of fermentation, a red blood cell concentrate, a platelet concentrate, a leukocyte concentrate, semen, red blood cells, and a recombinant protein-containing composition produced in a transgenic mammal. Preferably, the biological matrix is whole human blood or human blood plasma.

In a second aspect, the invention features a method of inactivating a contaminant of a biological matrix; the method includes the steps of: (a) contacting the biological matrix with an inactivating agent including an aziridino moiety, where a portion of the agent reacts with and inactivates the contaminant, and a portion of the agent remains unreacted; (b) contacting the product of step (a) with a quenching agent under conditions and for a time sufficient to allow the quenching agent to quench and to bond covalently to the unreacted inactivating agent; (c) contacting the product of step (b) with a solid support including at least 1 aldehyde moiety covalently bonded to the solid support, under conditions and for a time sufficient to allow the quenched inactivating agent to bond covalently to the aldehyde moiety; and (d) separating (i) the solid support, (ii) the quenched inactivating agent, and (iii) the quenching agent from the biological matrix, where the inactivating agent and the quenching agent are attached to the solid support through covalent bonds.

Preferred quenching agents include thiophosphate moieties and thiosulfate moieties. Preferably, the solid support contains at least 2 mmol/g aldehyde moieties attached to it.

In a third aspect, the invention features a method of quenching an electrophile; the method includes contacting the electrophile with a solid support including at least 1 thiophosphate moiety attached to the solid support through covalent bonds, under conditions and for a time sufficient to allow the electrophile to bond covalently to the thiophosphate moiety. The solid support preferably includes at least 2 mmol/g thiophosphate moieties, and more preferably includes at least 100 mmol/g thiophosphate moieties. In preferred methods, a plurality of the thiophosphate moieties are substituted with at least one $C_{1-12}$ saturated or unsaturated hydrocarbon skeleton that is unsubstituted or has between 1 and 4, inclusive, substituents, independently selected from the group consisting of hydroxyl, amino, cyano, and azido.

Preferably, the electrophile includes an aziridino moiety. For example, the electrophile may be ethyleneimine or an oligomer of ethyleneimine.

In a fourth aspect, the invention features a method of removing a viral inactivating agent from a biological matrix; the method includes the steps of: (a) contacting the inactivating agent with a quenching agent that is attached to a solid support through covalent bonds; and (b) removing the inactivating agent, the quenching agent, and the solid support from the biological matrix. Preferably, step (a) includes contacting the inactivating agent with the quenching agent under conditions and for a time sufficient to allow covalent bonds to form between the inactivating agent and the quenching agent. A preferred quenching agent includes a nucleophilic moiety, such as a thiophosphate moiety.

By "quenching moiety" or "a quenching agent" is meant a moiety or an agent that is capable of reacting with, and thereby reducing the reactivity of, an electrophilic compound.

By a "biological matrix" is meant a biological composition that contains biological macromolecules, such as proteins, nucleic acids, lipids, and carbohydrates.

The invention provides methods for quenching inactivating agents in a biological matrix. The resulting biological matrix is substantially free of infectious viruses; in addition, it does not contain remnants of the quenching agent or the quenched inactivating agent. The invention therefore provides purer products than can be obtained using conventional quenching techniques.

Other features and advantages of the invention will be apparent from the following description and from the claims.

DETAILED DESCRIPTION

Figure 1:
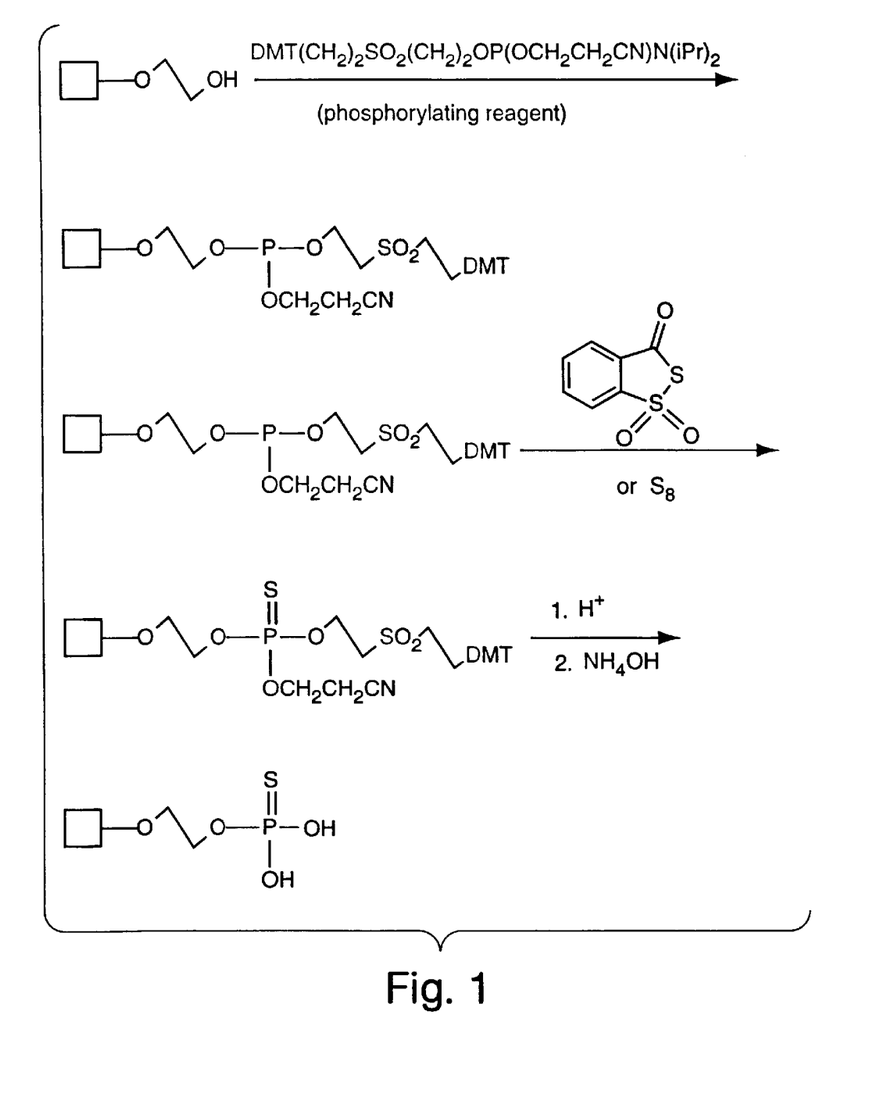
FIG. 1 is a scheme showing the preparation of a solid-phase quencher that contains a thiophosphate group.
Figure 2:
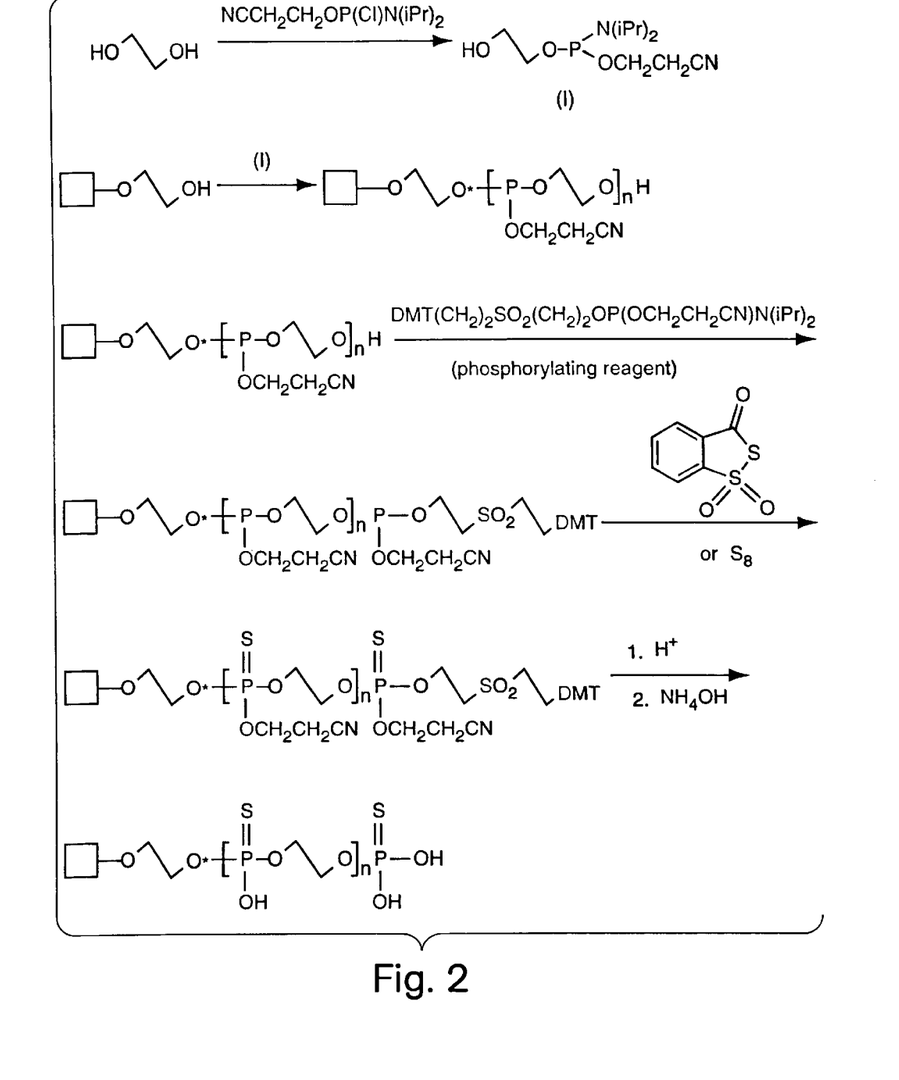
FIG. 2 is a scheme showing the preparation of a solid-phase quencher that contains multiple thiophosphate groups.
Figure 3:
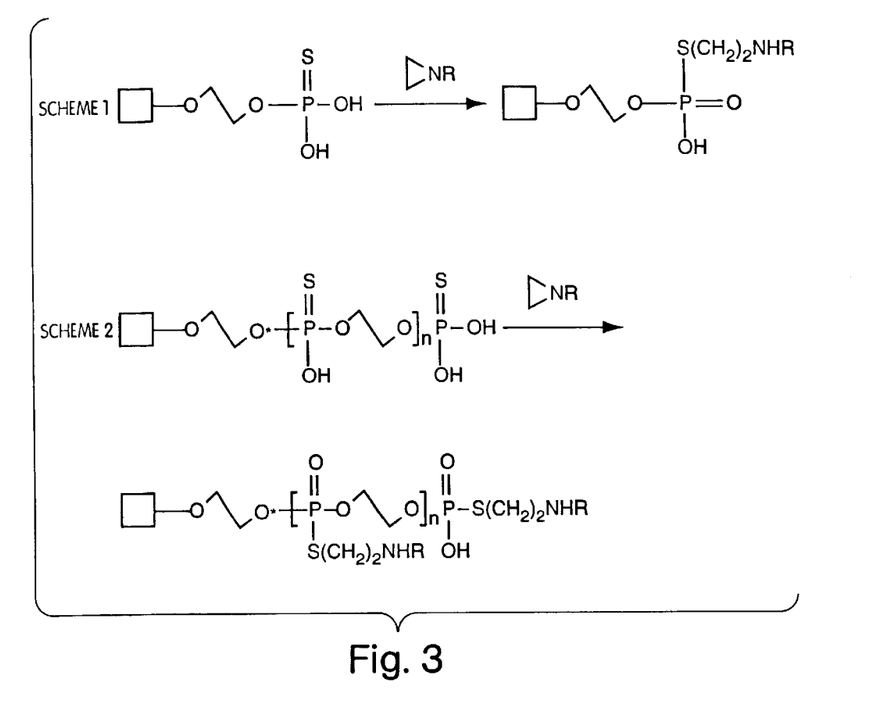
FIG. 3 is a scheme showing the quenching of an aziridino compound with a thiophosphate group that is covalently bonded to a solid support.
Figure 4:
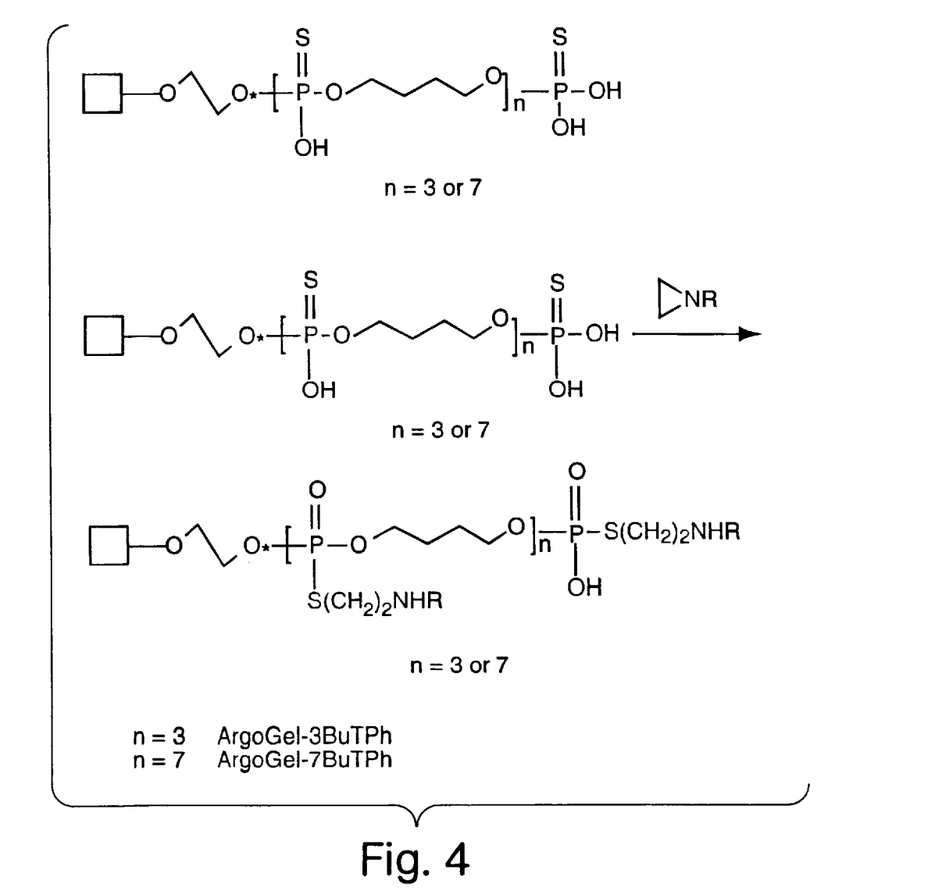
FIG. 4 is a scheme showing the quenching of an oligoethyleneimine with a solid-phase quencher containing phosphothio diester and phosphothio monoester groups.

The invention provides general methods for quenching electrophiles with quenching agents, such as thiophosphate moieties, that are attached to solid supports. Examples of such solid phase quenching systems are shown in FIGS. 1, 2, 3, and 4. A solid support containing a single thiophosphate moiety is shown in FIG. 1, and supports having a number of thiophosphate moieties attached to the support by covalent bonds are shown in FIGS. 2, 3, and 4.

The number of quenching moieties that can be attached to a support depends, in part, on the number of functional groups on the surface of the support. The total number of quenching moieties also depends on the number of quenching moieties attached to each functional group. For example, a polymeric support may contain 2 mmol/g hydroxyl groups; each of these hydroxyl groups can have as many as 150 thiophosphate groups attached to it. The solid support would therefore have 300 mmol/g thiophosphate groups.

The thiophosphate groups can be attached directly to the solid support, or they can be attached to the solid support through linkers. The linkers may have as many as 100 atoms. An example of a linking group is shown in FIG. 1; in this figure, the thiophosphate moiety is covalently bonded to an ethylene linker, which in turn is bonded to the solid support.

The thiophosphate groups themselves may also be separated by linkers. For example, as shown in FIG. 2, the thiophosphate groups are separated by ethylene chains. FIG. 4 shows a solid support in which the thiophosphate groups are separated by tetramethylene chains. In other embodiments of the invention, the thiophosphate groups may be separated by as many as 100 atoms.

A variety of materials can be used as the solid support. Examples of such materials include polymers (e.g., polyvinyl chloride, polytetrafluoroethylene), nylons (e.g., Dacron®), polyacrylamide pads deposited on solid surfaces, silicon, silicon-glass, and glass. The solid supports may be in any form suitable for use in the invention. For example, the solid supports may be in the form of beads, rods, or films; alternatively, the solid supports may be in the form of permeable and semi-permeable membranes. The solid support may be contained within a filtration device, such as a column or a cartridge.

Solid supports containing hydroxyl groups are commercially available, for example, from Argonaut Technologies, San Carlos, Calif. If the solid support does not have functional groups, such as hydroxyl or amino groups, on its surface, it can be derivatized. Any number of agents may be used to functionalize the solid support, as long as the end product is a solid support with a functional groups attached.

The thiophosphate groups used in the invention may be substituted with one substituent (e.g., [solid support]-OP(=S)(OH)$_2$, also referred to as a thiophosphomonoester), substituted with two substituents (e.g., [solid support]-OP(=S)(OH)(OAlk), a thiophosphodiester), or substituted with three substituents (e.g., [solid support]-OP(=S)(OAlk)$_2$, a phosphothiotriester). The substituent may be, for example, an unsubstituted alkyl group, or an alkyl group substituted with hydroxyl, amino, azido, or cyano groups.

Polythiophosphate moieties (i.e., moieties having 2 or more adjacent phosphate groups) can also be used in the invention. For example, guanosine diphosphate (GDP) or guanosine triphosphate (GTP), in which one or more of the phosphate groups is a thiophosphate group, may be used in the invention. In the case of guanosine diphosphate, one or both phosphate groups may be thiophosphate groups. In the case of guanosine triphosphate, one, two, or all three of the phosphate groups may be thiophosphate groups. GDP or GTP may be attached to the solid support, for example, at the 2' or the 3' hydroxyl group.

In addition, oligonucleotides (either DNA sequences or RNA sequences), in which one or more of the internucleotide linkages contain thiophosphate groups, can be attached to solid supports and used as quenching agents.

The compositions of the invention can be prepared as described below in the Examples. They can also be prepared using other standard synthetic techniques of oligonucleotide synthesis, such as those described in Oligonucleotides and Analogs A Practical Approach (Eckstein ed., IRL Press 1991).

As an example, the solid phase quenching systems of the invention can be used as follows. A viral inactivating agent, such as an ethyleneimine oligomer, is added to a biological matrix, as described in Budowsky, U.S. Pat. No. 6,136,586 and Budowsky et al., U.S. Pat. No. 6,093,564. At the end of the time necessary for viral inactivation, the biological matrix is contacted with a solid support containing thiophosphate groups. The matrix and the solid support are allowed to remain in contact for at least one hour, at room temperature and a pH of 7. A 10-fold excess of thiophosphate groups per equivalent of ethyleneimine oligomer is used.

The support can be added to the matrix in the form of particles; these particles can be removed, for example, by filtration after the inactivating agent is quenched. Alternatively, the biological matrix can be passed through a filtration device, such as a column that contains support-bound thiophosphate groups.

The thiophosphate groups react with the highly reactive aziridino moieties of the ethyleneimine compounds and remain covalently bonded to the ethyleneimine compounds, as shown in FIGS. 3 and 4. When the solid support-bound thiophosphate groups are removed from the biological matrix, therefore, the quenched ethyleneimine compounds are removed as well. The end result is a biological matrix that is substantially free of infectious viruses, quenched ethyleneimine compounds, and quenching agent.

Another way to obtain biological matrices free of infectious viruses, quenched inactivating agent, and quenching agent is to inactivate viruses in the matrices with an inactivating agent, such as ethyleneimine dimer, as described above. After the viruses have been inactivated, the inactivating agent can be quenched with a traditional quenching agent, such as sodium thiosulfate. A solid support containing an electrophilic group can then be added; reactive groups on the support form covalent bonds with the quenched inactivating agent. The quenched inactivating agent and the quenching agent can then be easily removed from the matrix, as they are attached to the solid support through covalent bonds.

For example, a biological matrix containing the inactivating agent ethyleneimine dimer can be quenched with sodium thiosulfate. Methods for inactivating viruses in biological matrices and quenching with thiosulfate are well known in the art and are described, for example, in Budowsky, U.S. Pat. No. 5,891,705. The thiosulfate reacts with the aziridine ring and remains covalently bound to the quenched ethyleneimine dimer.

A solid support having aldehyde groups can then be added to the reaction mixture. Such supports are commercially available from a number of sources, including Argonaut Technologies. The support and the matrix are allowed to remain in contact for at least one hour, at room temperature and a pH of 7. A 10-fold excess of aldehyde groups per equivalent of ethyleneimine dimer is used. The aldehyde moieties react with the primary amino groups of the dimers to form relatively stable imine complexes; the quenched inactivating agent, as well as the thiosulfate moiety, therefore remains covalently bonded to the solid support. The solid support can be removed from the matrix, for example by filtration, along with the quenched inactivating agent and the quenching agent.

The biological matrix may include any of a number of substances. Examples of matrices include whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture medium, a placental extract, a product of fermentation, a red blood cell concentrate, a platelet concentrate, a leukocyte concentrate, semen, and red blood cells. Other biological matrices include those containing recombinant proteins produced in transgenic mammals. For example, the biological matrix may include a protein that has been expressed in the milk of a transgenic mammal. Methods for producing such proteins are described, for example, in Wright et al., *BioTechnology* 9:830–834 (1991) and the references cited therein.

There now follow particular examples that describe the preparation of solid phase quenching systems of the invention and the use of these systems to quench viral inactivating agents. These examples are provided for the purpose of illustrating the invention, and should not be construed as limiting.

EXAMPLE 1
Preparation of a Solid-phase Quencher that Contains a Thiophosphate Group The preparation of a solid phase quencher of the invention is described in FIG. 1. As shown there, a solid support (designated with a square) containing a hydroxyl group is derivatized with a phosphorylating agent. The phosphite group of the phosphorylated solid support is oxidized to form a thiophosphate ester, which is cleaved with acid to provide a thiophosphate moiety. The product is a thiophosphate moiety that is attached to a solid support through covalent bonds.

EXAMPLE 2
Preparation of a Solid-phase Quencher that Contains Multiple Thiophosphate Groups The preparation of a solid support with a high loading of thiophosphate groups is shown in FIG. 2. As shown there, ethylene glycol is derivatized to yield a monomer (I) containing a phosphoramidite group. This monomer is polymerized, using a solid support containing an hydroxyl group as an initiator (available from Argonaut Technologies). The resulting polymer is phosphorylated, then oxidized to yield a solid support that contains multiple thiophosphate esters. The esters are cleaved with acid, resulting in a solid support that has (n+1) thiophosphate moieties attached to it.

EXAMPLE 3
Quenching of an Aziridino Compound with a Thiophosphate Group that is Bound to a Solid Support As shown in FIG. 3, Scheme 1, a nucleophilic thiophosphate group, which is bound to a solid support, attacks and quenches the aziridino compound; the aziridino compound is not only rendered inactive, it also remains bonded to the solid support through covalent bonds.

As shown in FIG. 3, Scheme 2, a solid support with (n+1) thiophosphate groups attached is capable of quenching (n+1) aziridino moieties.

EXAMPLE 4
Quenching of Oligoethyleneimine with Solid-phase Quenchers Containing Phosphothio Diester and Phosphothio Monoester Groups As shown in FIG. 4, thiophosphate groups on the solid support are separated by chains containing 4 atoms. When the solid support is contacted with a composition containing ethyleneimine oligomers, all of the thiophosphate groups on the solid support can react with the oligomers.

Figure 5:
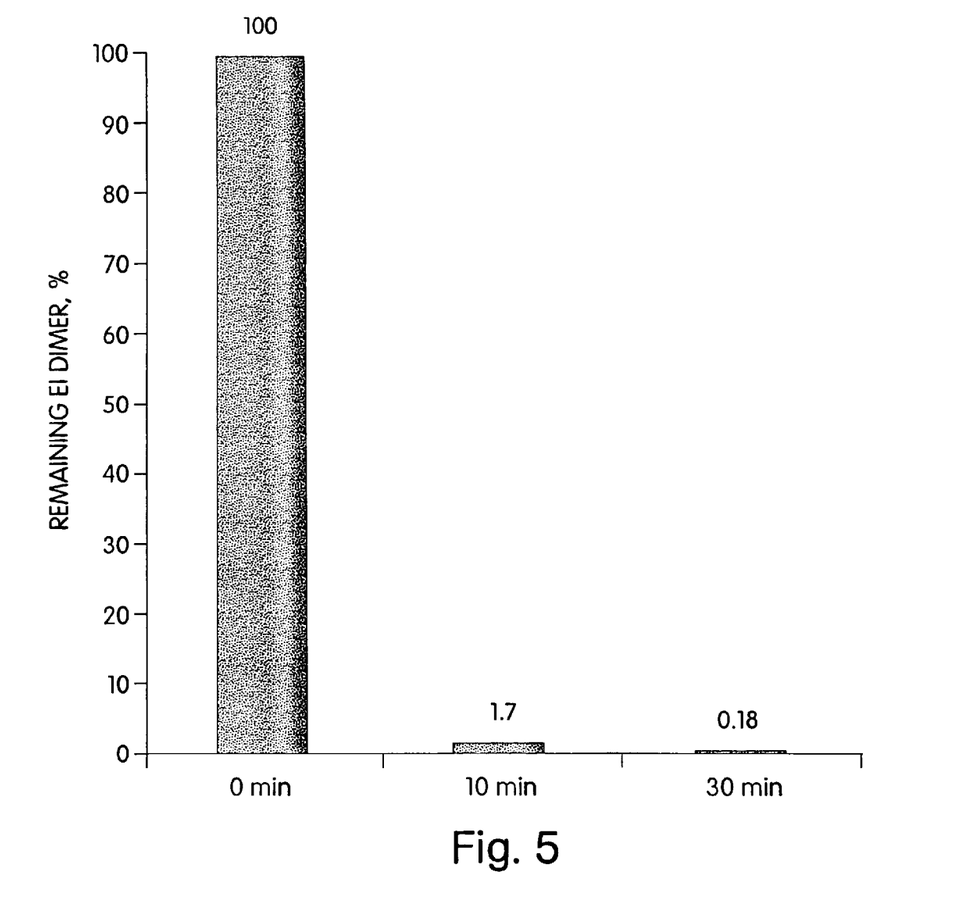
FIG. 5 is a graph showing the quenching of ethyleneimine dimer in whole CPD human blood using a solid-phase quencher.

EXAMPLE 5
Quenching of Ethyleneimine Dimer with Solid Phase Quencher Containing Thiophosphomonoester Groups 200 $\mu$l of 100 mM MOPS buffer (pH 7.0) containing 12 mM ethyleneimine dimer (2.4 $\mu$mole total) were added to 25 mg (20 $\mu$mole-equivalents of thiophosphate groups) of ArgoPore-thiophosphate solid phase support (prepared as described in Example 2). The loading of phosphothiomonoester groups on the ArgoPore-thiophosphate support was about 0.8 mmole/mg. The reaction mixture was incubated, with agitation, for 30 minutes at 23° C. Two aliquots (5 $\mu$l) of the solution were removed after 10 and 30 minutes of incubation, and the concentration of the remaining ethyleneimine dimer was determined by HPLC (FIG. 5). As shown there, only 0.18% of the dimer remained in the solution after 30 minutes. This example demonstrates the ability of the support-bound thiophosphate groups to inactivate ethyleneimine dimers.

EXAMPLE 6
Quenching of Ethyleneimine Dimer in Whole CPD Human Blood Using a Solid-phase Quencher 50 µl of 120 mM ethyleneimine dimer (EID, PEN102) in 0.25 M $NaH_2PO_4$ was added to 0.9 ml of whole human CPD blood (final concentration of EID was 6 mM, 6 µmole total), and incubated at 23° C. for 4 hours. At the end of the 4-hour incubation period, 68 mg (50 µmole-equivalents of phosphothiomonoester groups) of ArgoPore-Thiophosphate support (prepared as described in Example 2) was added. In the parallel experiment, 50 µl of 1 M $Na_2S_2O_3$ (final concentration 50 mM) was added to same amount of EID treated blood. Both samples were allowed to incubate for 2 hours at 23° C. The red blood cell (RBC) and plasma fraction of the blood were separated by centrifugation (10,000 rpm, 5 min), and the RBCs were opened by adding 9 volumes of water. The concentration of EID was determined in the RBC fraction and in the plasma fraction of the blood by HPLC (FIG. 6).

Figure 6:
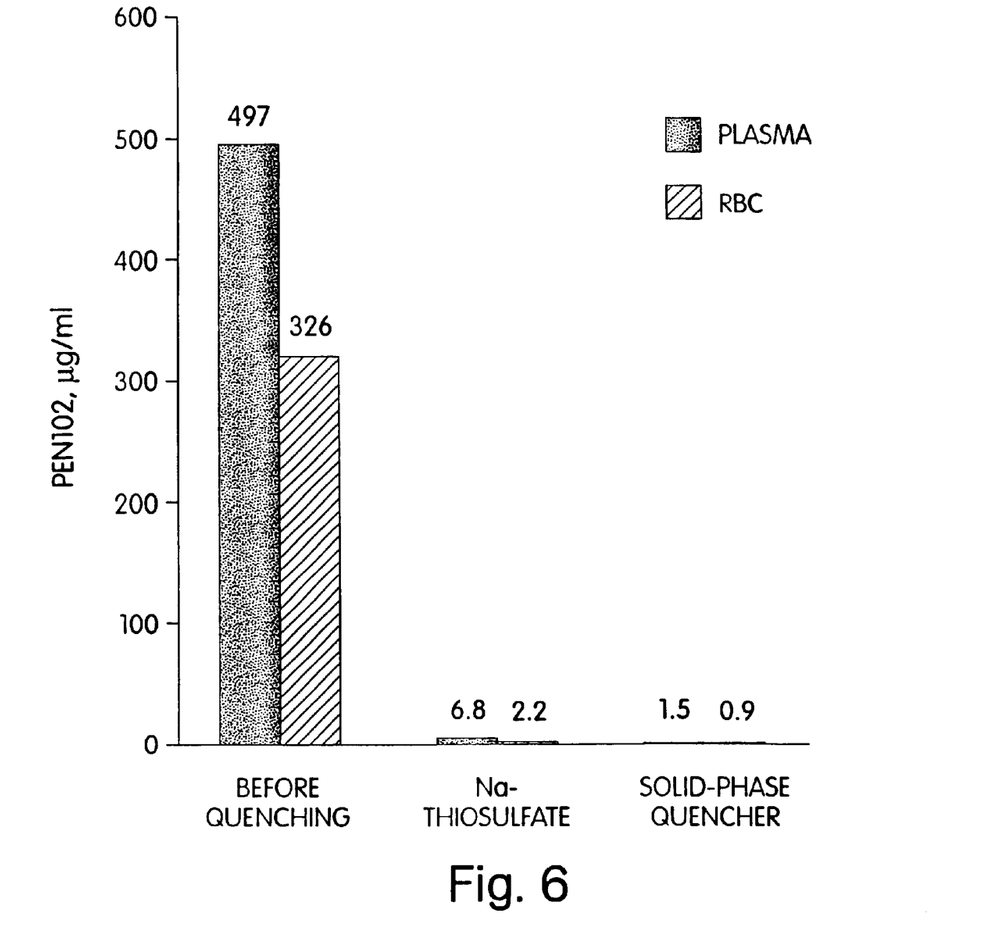
FIG. 6 is a graph showing the quenching of ethyleneimine dimer with a solid phase quencher containing thiophosphomonoester groups.

As shown in FIG. 6, both sodium thiosulfate and solid phase-bound thiophosphate groups were capable of quenching ethyleneimine dimer. After 2 hours, the plasma quenched with thiosulfate contained only 6.8 µg/ml dimer, and the red blood cells quenched with thiosulfate contained 2.2 µg/ml dimer. The solid phase quencher containing thiophosphate groups was even more effective. The plasma quenched with this system contained only 1.5 µg/ml dimer, and the red blood cells contained only 0.9 µg/ml dimer after 2 hours.

Figure 7:
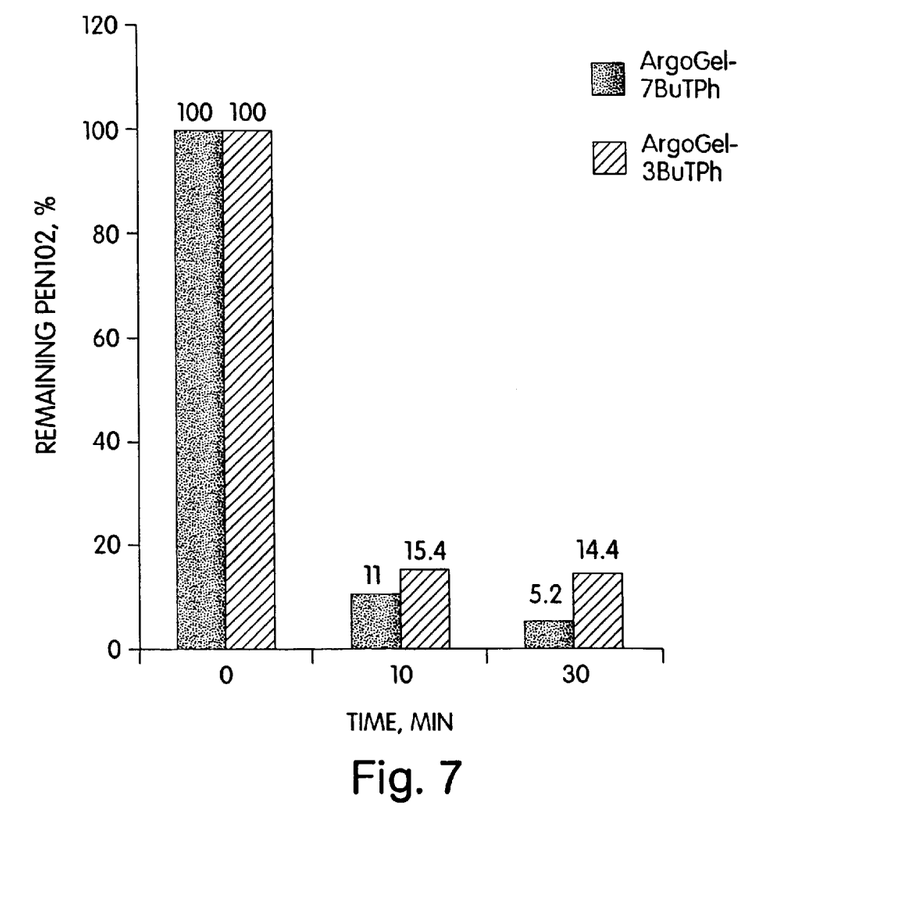
FIG. 7 is a graph showing the quenching of ethyleneimine dimer with solid phase quenchers containing thiophosphodiester and thiophosphomonoester groups.

EXAMPLE 7
Quenching of Ethyleneimine Dimer with Solid Phase Quencher Containing Thiophosphodiester and Thiophosphomonoester Groups 200 µl of 100 mM MOPS buffer (pH 7.0) containing 12 mM ethyleneimine dimer (PEN102, 2.4 µmole total) were added to 10 mg (20 µmole-equivalent of thiophosphate groups) of ArgoGel-7BuTPh or 21 mg (20 µmole-equivalent of thiophosphate groups) of ArgoGel-3BuTPh solid phase support (shown in FIG. 4). The reaction mixture was incubated, with agitation, for 30 minutes at 23° C. Two aliquots (5 µl each) of the solution were removed after 10 and 30 minutes of incubation, and the concentration of the remaining ethyleneimine dimer was determined by HPLC (FIG. 7).

As shown there, both the ArgoGel-3BuTPh and the ArgoGel-7BuTPh systems were effective in quenching the ethyleneimine dimer. When ArgoGel-7BuTPh was used, only 11% of the dimer remained after 10 minutes, and 5.2% remained after 30 minutes. When ArgoGel-3BuTPh was used, 15.4% remained after 10 minutes, and 14.4% remained after 30 minutes.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A method of quenching an electrophile, said method comprising contacting said electrophile with a solid support comprising at least 1 thiophosphate moiety attached to said solid support through covalent bonds, under conditions and for a time sufficient to allow said electrophile to bond covalently to said thiophosphate moiety.

2. The method of claim 1, wherein said solid support comprises at least 2 mmol/g thiophosphate moieties.

3. The method of claim 1, wherein said solid support comprises at least 100 mmol/g thiophosphate moieties.

4. The method of claim 1, wherein a plurality of said thiophosphate moieties are substituted with at least one $C_{1-12}$ saturated or unsaturated hydrocarbon skeleton that is unsubstituted or has between 1 and 4, inclusive, substituents, independently selected from the group consisting of hydroxyl, amino, cyano, and azido.

5. The method of claim 1, wherein said electrophile comprises an aziridino moiety.

6. The method of claim 1, wherein said electrophile is ethyleneimine.

7. The method of claim 1, wherein said electrophile is an oligomer of ethyleneimine.

* * * * *